United States Patent
Beste et al.

(10) Patent No.: US 6,503,869 B1
(45) Date of Patent: Jan. 7, 2003

(54) ENHANCED POST-EMERGENT HERBICIDAL COMPOSITIONS CONTAINING AMMONIUM SALTS AND METHODS OF USING THE SAME

(75) Inventors: C. Edward Beste, Rehoboth, DE (US); Mike A. Priola, Millsboro, DE (US); Robert A. Smiley, Wilmington, DE (US)

(73) Assignee: Falcon Lab LLC, Wilmington, DE (US)

( * ) Notice: Subject to any disclaimer, the term of this patent is extended or adjusted under 35 U.S.C. 154(b) by 0 days.

(21) Appl. No.: 09/932,905

(22) Filed: Aug. 20, 2001

Related U.S. Application Data

(60) Provisional application No. 60/226,516, filed on Aug. 21, 2000.

(51) Int. Cl.$^7$ .................. A01N 37/02; A01N 37/06; A01N 43/82; A01N 47/36; A01N 57/02
(52) U.S. Cl. ............. 504/127; 504/135; 504/136; 504/139; 504/142
(58) Field of Search .................. 504/127, 118, 504/129, 139, 135, 136, 142

(56) References Cited

U.S. PATENT DOCUMENTS

| | | | |
|---|---|---|---|
| 4,975,110 A | 12/1990 | Puritch et al. ............. 504/142 |
| 4,975,113 A * | 12/1990 | Marrs et al. ................ 71/121 |
| 5,035,741 A | 7/1991 | Puritch et al. ............. 504/142 |
| 5,098,467 A | 3/1992 | Puritch et al. ............. 504/142 |
| 5,098,468 A | 3/1992 | Puritch et al. ............. 504/142 |
| 5,106,410 A | 4/1992 | Puritch et al. ............. 504/142 |
| 5,196,044 A | 3/1993 | Caulder et al. ............ 504/127 |
| 5,298,480 A * | 3/1994 | Watson et al. ............. 504/213 |
| 5,683,959 A | 11/1997 | Caulder et al. ............ 504/127 |
| 5,700,759 A | 12/1997 | Caulder et al. ............ 504/133 |
| 5,703,019 A | 12/1997 | Evans et al. .............. 504/320 |
| 5,872,078 A | 2/1999 | Kuchikata et al. ......... 504/206 |
| 5,919,733 A | 7/1999 | Sedun et al. .............. 504/320 |
| 5,919,734 A | 7/1999 | Jones ...................... 504/320 |
| 5,948,731 A | 9/1999 | Evans et al. .............. 504/320 |
| 5,994,269 A | 11/1999 | Bugg et al. ............... 504/127 |
| 5,998,332 A | 12/1999 | Sato et al. ................ 504/127 |
| 6,034,034 A | 3/2000 | Caulder et al. ............ 504/130 |
| 6,136,856 A | 10/2000 | Savage et al. ............. 514/552 |
| 6,218,336 B1 | 4/2001 | Coleman .................. 504/118 |
| 6,228,807 B1 * | 5/2001 | Kuchikata et al. ......... 504/206 |
| 6,323,156 B1 | 11/2001 | Smiley ..................... 504/320 |

\* cited by examiner

*Primary Examiner*—S. Mark Clardy
(74) *Attorney, Agent, or Firm*—Locke Liddell & Sapp LLP

(57) ABSTRACT

A method for enhancing the effectiveness of post-emergent herbicides consists of the addition, to the post-emergent herbicidal composition, of an effective amount of a compound of the formula $R_1COO^-X^+$ (I) wherein $R_1$ is a $C_7$ to $C_{11}$ hydrocarbyl group optionally substituted with one or more hydroxyl or $C_1$–$C_5$ hydrocarbyl groups, and X is ammonium. The advantages of using a compound of formula (I) with the post-emergent herbicide include a faster visual phytotoxic response, better weed control and use of less post-mergent herbicide.

33 Claims, No Drawings

US 6,503,869 B1

ENHANCED POST-EMERGENT HERBICIDAL COMPOSITIONS CONTAINING AMMONIUM SALTS AND METHODS OF USING THE SAME

This application claims priority to provisional application serial No. 60/226,516, filed Aug. 21, 2000.

FIELD OF THE INVENTION

A means of enhancing the effectiveness of post-emergent herbicides comprises the addition of an effective non-herbicidal amount of an ammonium salt of a $C_7$–$C_{11}$ aliphatic monocarboxylic acid to a post-emergent herbicide.

BACKGROUND OF THE INVENTION

Herbicides are generally classified into two groups— those having significant foliar use and those primarily applied into the soil. Herbicides with significant foliar use, generally described as post-emergent herbicides, are further divided into three major categories based on translocation patterns and initial plant symptoms: (a) translocated herbicides showing initial symptoms on new growth; (b) translocated herbicides showing initial symptoms on older growth; and (c) non-translocated herbicides showing initial localized injury. Each of these categories may further be subdivided according to herbicidal mode of action, i.e., auxin-type growth regulators; aromatic amino acid (EPSDS) inhibitors; branched-chain amino acid (ALS/AHAS) inhibitors; carotenoid pigment inhibitors; lipid biosynthesis (ACCase) inhibitors; organic arsenicals; "classical" photosynthesis inhibitors; "rapidly acting" photosynthesis inhibitors; Photosystem I (PSI) energized cell membrane destroyers; protoporphyrinogen oxidase [Protox (PPO)] inhibitors; and glutamine synthesis inhibitors. Of these, the most popular are glyphosate and salts of glyphosate including the monoammonium, diammonium and isopropyl ammonium salts disclosed in U.S. Pat. Nos. 5,998,332; 4,507,250; 4,481,026; 4,405,531; 4,315,765; 4,140,513; 3,977,860; 3,799,580; and 3,853,530 (including the commercial products Roundup® and Touchdown®), sulfonylurea, (sold under the tradename Classic® by E.I. duPont de Nemours and Co.), glufosinate, first reported as a herbicide in Schwerdtle,: et. al. "Z. Pflanzenkr. Pfanzenschutz. Sonderheft IX. p. 431 (and now including the commercial product Finale®), oxyfluorfen, disclosed in U.S. Pat. No. 3,798,276 (and now commercially sold as Goal®), imazamox, discovered by American Cyanamid (now commercially available as Raptor®), clethodim, first reported by Kincade, et. al. in Proc. Br. Crop Prot. Conf. Weeds in 1987 (now commercially sold as Select®), sethoxydim, discovered by Nippon Soda in Japan (now commercially sold as Poast®), quizalofop, disclosed in U.S. Pat. No. 4,629,493 (now commercially sold as Assure®), fenoxaprop, first reported by Bieringer, et. al. in Proc. Br. Crop Prot. Conf. Weeds in 1982 (now commercially sold as Fusion® and Acclaim), fluazifop, disclosed in British Patent 1,599,121 (now commercially sold as Horizon 2000 and Fusilade DX) and bipyridilium salts first disclosed in British Patent 813,531 (commercially sold as Paraquat® and Diquat®) amongst others.

Post-emergent herbicides are generally slow-acting and usually take days or even weeks to show a visual effect on the weeds and grasses to which they have been applied.

This is undesirable from the user's standpoint.

Accordingly, it is desirable to provide enhanced herbicidal compositions containing a post-emergent herbicide, methods for enhancing the activity of existing herbicides and methods of controlling plant growth in order to overcome the inadequacies of the prior art.

A recent advance is disclosed in U.S. Pat. No. 5,994,269 which is directed to the addition of a water soluble salt to glyphosate. However, the time to achieve the reported visual herbicidal effect is long. Along with the need to obtain a faster time for visualization of the herbicidal effect, it is further desired to develop a means which mandates less of the herbicidal active ingredient than is now employed. The reduction in the amount of the herbicidal active ingredient is desired since such chemicals are generally toxic and. non-biodegradable.

SUMMARY OF THE INVENTION

It has been discovered that the herbicidal activity of post-emergent herbicides is enhanced by the addition, to the post-emergent herbicide, of an ammonium salt of an aliphatic carboxylic acid. Such salts permit utilization of reduced amounts of the active ingredient while still providing effective weed control. Additionally, use of the composition of the invention reduces the time required for systemic phytotoxic symptoms to appear on the target weed.

The ammonium salt is a compound of the formula:

$$R_1COO^-X^+ \qquad (I)$$

wherein $R_1$ is a $C_7$ to $C_{11}$ hydrocarbyl group and X is ammonium ($NH_4^+$). In the formula (I), any of the hydrogen on $R_1$ may be substituted with one or more hydroxyl or $C_1$–$C_5$ hydrocarbyl group, such as an alkyl group. In a preferred embodiment, the compound of formula (I) is ammonium pelargonate, a highly water soluble salt which has low toxicity and high biodegradability.

DETAILED DESCRIPTION OF PREFERRED EMBODIMENTS

The effectiveness of post-emergent herbicides is dramatically improved by addition of a compound of formula (I) to a post-emergent herbicide prior to its application to the vegetation. The compound of formula (I) is represented by the formula:

$$R_1COO^-X^+ \qquad (I)$$

wherein $R_1$ is a saturated or unsaturated $C_7$ to $C_{11}$ hydrocarbyl group, X is ammonium ($NH_4^+$) and any of the hydrogen on $R_1$ may be substituted with one or more hydroxyl or $C_1$–$C_5$ hydrocarbyl groups.

The composition applied to the vegetation of the invention may further contain a diluent. Any solvent in which formula (I) is soluble may be employed as a diluent. As a post-emergent, the herbicidal compositions of the invention are preferably applied to the locus of the unwanted vegetation as an aqueous solution.

When a compound of the formula (I) is added to a post-emergent herbicidal composition
 (a) either as a water solution or as a solid or
 (b) by diluting a commercial herbicidal concentrate to a herbicidally effective concentration [with a water solution of formula (I)]
and the resulting mixture is applied to weeds according to the herbicide manufacturers recommendation, the weeds exhibit a visual phytotoxic effect in less time than would be obtained with the herbicide in the absence of the compound of formula (I). As an example, weed and grass necrosis may approach 100% within 24 hrs. with glyphosate in combination with ammonium pelargonate, compared to 3–4 days or longer without the ammonium pelargonate.

Furthermore, with the addition of a compound of formula (I) such as ammonium pelargonate to the post-emergent herbicide, less of the post-emergent herbicide than specified by the manufacturer can be used to achieve the same herbicidal result as would be obtained using the herbicide suppliers' recommended amount in the absence of ammonium pelargonate.

The herbicidal composition of the invention containing a compound of formula (I) may be applied to the locus of the unwanted vegetation in effective amounts in the manner normally used with the herbicide without the addition of the compound of formula (I). Concentrations of the post-emergent herbicide in the herbicidal composition of the invention will vary depending on the herbicide and the weeds to be controlled but the concentration of the compound of formula (I) in the final herbicidal composition is preferably between from about 0.10 to about 3.0% by weight of the herbicidal composition, preferably between from about 0.5% to about 1.0% by weight. The "final herbicidal composition" refers to the composition actually applied to the unwanted vegetation.

This preferred amount of compound of formula (I) is independent of the selection of post-emergent herbicide in the composition. Thus, regardless if. the post-emergent herbicide is a sulfonyl urea, which typically is used in amounts approximating 5 to 10 grams per acre, or glyphosate, which typically is used in agricultural sprays in amounts approximating 0.75 to 1.0 weight percent, the amount of compound of formula (I) in the final herbicidal composition is between from about 0.10 to about 3.0 weight percent of the herbicidal composition.

Any post-emergent herbicide, regardless of its mode of action, may be used in combination with the ammonium salt of formula (I). These include those translocated herbicides showing initial symptoms on new growth (Table I); translocated herbicides showing initial symptoms on older growth (Table II); and non-translocated herbicides showing initial localized injury (Table III), as set forth in Ross and Lembi, *Applied Weed Science*, 2d edition, Prentice-Hall, 1999, pp. 156–157:

TABLE I

| TYPE | TRADENAME |
| --- | --- |
| Auxin-Type Growth Regulators Phenoxy acid herbicides | |
| 2,4-D | Numerous |
| 2,4-DB | Butoxone, Butyrac |
| 2,4-DP (dichlorprop) | Available only in mixtures |
| MCPA | Rhonox, Rhomene, Sword, Weedon MCPA |
| MCPB | Thistrol |
| MCPP (mecoprop) | MCPP 4K, Mecomec |
| Benzoic acid herbicides | |
| Dicamba | Banvel, Clarity, Vanquish |
| Picolinic acid (pyridinecarboxylic) herbicides and relatives | |
| Clopyralid | Lontrel, Reclaim, Stinger, Transline |
| Picloram | Tordon |
| Triclopyr | Garton, Grandstand, Remedy, Turflon |
| No chemical family recognized | |

TABLE I-continued

| TYPE | TRADENAME |
| --- | --- |
| Naptalam | Alanap |
| Aromatic Amino Acid (EPSPS) inhibitors | |
| Glyphosate | Accord, Rodeo, Roundup, Roundup Ultra, Touchdown (sulfosate) |
| Branched-Chain Amino Acid (ALS/AHAS) Inhibitors Sulfonylurea herbicides | |
| Bensulfuron | Londax |
| Chlorimuron | Classic |
| Chlorsulfuron | Glean, Telar |
| Halosulfuron | Manage, Permit |
| Metasulfuron | Ally, Escort |
| Nicosulfuron | Accent |
| Primisulfuron | Beacon |
| Prosulfuron | Peak |
| Rimsulfuron | Matrix |
| Sulfometuron | Onst |
| Thifensulfuron | Pinnacle |
| Triasulfuron | Amber |
| Tribenuron | Express |
| Triflusulfuron | UpBeet |
| Imidazolinone herbicides | |
| Imazamethabenz | Assert |
| Imazamox | Raptor |
| Imazapic | Cadre, Plateau |
| Imazapyr | Arsenal, Chopper, Stalker |
| Imazaquin | Scepter, Image |
| Imazethepyr | Pursuit |
| Triezolopyrimidine sulfonanilide herbicides | |
| Cloransulam | FirstRate |
| Flumetsulam | Broadstrike, Python |
| Pyrimidinyl oxybenzoate herbicides | |
| Pyrithlobac | Staple |
| Carotenoid Pigment inhibitors No chemical family recognized | |
| Amitrole | Amitrol-T |
| Clomazone | Command |
| Fluridone | Sonar |
| Isoxazole herbicide | |
| Isoxaflutole | Balance |
| Pyridazinone herbicide | |
| Norflurazon | Predict, Solicam, Zorial |
| Lipid Biosynthesis (ACCase) Inhibitors | |
| Aryloxyphenoxy propionate herbicides | |
| Diclofop | Hoelon |
| Fenoxaprop | Acclaim, Whip 1EC |
| Fenoxaprop-P | Acclaim Extra, Option II, Whip 360 |
| Fluazifop-P | Fusilade II, Fusilade DX, Omamic 170 |
| Haloxyfop | Verdict, Gallant |
| Quizalofop-P | Assure II |
| Cyclohexanedione herbicides | |
| Clethodim | Envoy, Prism, Select |
| Sethoxydim | Poast, Poast Plus, Prestige, Torpedo, Ultima, Vantage |
| Tralkoxydim | Achieve |
| Organic Arsenicals | |
| DSMA | Ansar, DSMA Liquid |
| MSMA | Ansar, Arsenate Liquid, Bueno, |

TABLE I-continued

| TYPE | TRADENAME |
|---|---|
| | Daconate |
| Unclassified Herbicides | |
| Asulam | Asulox |
| Difenzoquat | Avenge |
| Fosamine | Krenite |
| Propanil | Stam; Stampede |

TABLE II

| "Classical" Photosynthesis Inhibitors S-Triazine herbicides | |
|---|---|
| Ametryn | Evik |
| Atrazine | Aatrex, Atrazine |
| Cyanazine | Bladex |
| Hexazinone | Velpar |
| Prometon | Pramitol |
| Prometryn | Caparol |
| Simazine | Princep |
| as-Triazine herbicide | |
| Metribuzin | Lexone, Sencor |
| Phenylurea herbicides | |
| Diuron | Kamex |
| Fluometuron | Cotoran |
| Linuron | Lorox |
| Tebuthiuron | Spike |
| Uracil herbicides | |
| Bromacil | Hyvar |
| Terbacil | Sinbar |
| "Rapidly Acting" Photosynthesis Inhibitors Benzothiadiazole herbicide | |
| Bentazon | Basagran |
| Benzonitrile herbicide | |
| Bromoxynil | Buctril |
| Phenylcarbamate herbicides | |
| Desmedipham | Betanex |
| Phenmedipham | Spin-Aid |
| Pyridazinone herbicide | |
| Pyrazon | Pyramin |
| Phenylpyridazine herbicide | |
| Pyridate | Tough |

TABLE III

| Photosystem I (PS I) Energized Cell Membrane Destroyers Bipyridilium herbicides | |
|---|---|
| Paraquat | Cyclone, Gramoxone Extra, Starfire |
| Diquat | Diquat, Reward |
| Protoporphyrinogen Oxidase [Protox (PPO)] Inhibitors Diphenylether herbicides | |
| Acifluorfen | Blazer, Status |
| Fomesafen | Flexstar, Reflex |
| Lactofan | Cobra |
| Oxyfluorfen | Goal |
| Oxadiazole herbicides | |
| Oxadiazon | Ronstar |
| Fluthiacet | Action |

TABLE III-continued

| N-phenylphthalimide herbicide | |
|---|---|
| Flumiclorac | Resource |
| Triazolinone herbicides | |
| Carfentrazone | Affinity, Aim |
| Sulfentrazone | Authority, Cover, Spartan |
| Glutamine Synthesis Inhibitors | |
| Glufosinate | Finale, Liberty, Rely |

Particularly desirable results have been evidenced in herbicidal compositions containing the compound of formula (I) and glyphosates (N-phosphonomethylglycines) and ammonium (particularly monoammonium and diammonium) salts thereof; sulfonyl urea herbicides, especially rimsulfuron containing herbicides; cyclohexanediones, such as sethoxydim containing herbicides; benzothiadiazole herbicides; diphenylether herbicides especially those containing fomesafen; and bipyridilium herbicides, such as paraquat and diquat.

The method of the invention may be used to control established vegetation in the vicinity of a seeded crop or in a weed concentrate area by contacting the foliage of the unwanted vegetation with the herbicidal composition.

Surfactants, wetting agents, dispersing agents, suspending agents, and/or emulsifying agents may further be employed with the herbicidal composition of the invention. Such materials are typically included in commercial herbicidal formulations, to which may be added the compound of formula (I).

Unwanted vegetation may be killed by applying to the locus of the vegetation the herbicidal composition of the invention. The herbicidal composition of the invention may be contacted with the unwanted vegetation by spraying or otherwise distributing the composition onto the foliage in accordance with the manufacturers' directions of the post-emergent herbicide [to which has been added the compound of formula (I)]. The herbicides of the invention exhibit several advantages not previously seen with other commercial herbicides. Most importantly, the invention dramatically reduces the kill time. Leaves of vegetation sprayed with herbicidal compositions of the invention usually start to shrivel or turn brown within hours of a single application. Necrosis is evident, usually in 24 hours. Typically unwanted vegetation is dead in less than 24 hours compared to 3 to 4 days when the post-emergent is solely used. Since use of the compound of formula (I) decreases the amount of post-emergent herbicide required, the invention dramatically reduces costs.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLES

The following non-limiting examples, and comparative demonstrations, bring out the more salient features of this invention. All parts are given in terms of weight units except as may otherwise be indicated.

Example 1

Two 24 fluid oz. spray bottles of commercial ready-to-use ROUNDUP were obtained having a glyphosate content (in the form of its isopropylamine salt) of about 0.96%. From one bottle, 61 ml. of the contents were removed and replaced by 61 g. of a 33% by weight solution of ammonium pelargonate. This gave a final concentration of 0.87% glyphosate salt and 3.0% ammonium pelargonate. From the other bottle 61 ml. of the contents were removed and replaced with 61 ml. of water. Thus the glyphosate salt concentration in the second bottle was also 0.87%.

A plot of ground 2 ft. by 3 ft. containing grass species, crabgrass, clover, woodsorrel and other weeds was sprayed with the Roundup containing no added ammonium pelargonate. A similar adjacent plot was sprayed with the ROUNDUP containing ammonium pelargonate. Within 24 hrs the plot sprayed only with ROUNDUP showed little change in color although a few weeds were wilting. In the second plot sprayed with ROUNDUP and ammonium pelargonate, the entire plot had turned brown with many of the weeds completely shriveled up. After 14 days, all of the vegetation on both plots were dead showing that the ammonium pelargonate had a synergistic effect and that it did not affect the herbicidal properties of the ROUNDUP but only enhanced the rate of kill.

Example 2

A field study was made on fescue suppression (fescue thatch, 9–10 in. height, blade length 10–16 in.) using a 0.2% by weight solution of ammonium pelargonate alone, glyphosate ammonium salt alone (ROUNDUP DF®) at application rates of both 0.21 lb. active ingredient/acre (ai/A) and 0.42 lb. ai/A and a combination of 0.2% ammonium pelargonate with the same rates of ROUNDUP DF. The spray rate was 15 gal./acre (gpa) in all cases. One week after spraying, the following results were obtained:
Ammonium Pelargonate
The necrosis was 0%, i.e. no vegetation was killed.
ROUNDUP DF
The necrosis was 17% at the 0.21 lb. rate while at 0.42 lb./acre the observed necrosis was 40%.
Ammonium Pelargonate Plus ROUNDUP DF
With a combination of 0.21 lb./acre ROUNDUP prepared in 0.2% ammonium pelargonate solution, the necrosis was 40%, a 2.35 times better control rate. At 0.5 lb./acre ROUNDUP in 0.2% ammonium pelargonate solution, the necrosis was 60%, or 1.5 times better control.

Example 3

A second field study was made on fescue suppression using glyphosate ammonium salt (ROUNDUPO DF) and a combination of ammonium pelargonate with the glyphosate. The glyphosate alone (control) was applied at a rate of 0.32 lb./acre while the combination was 0.32 lb/acre glyphosate in a 2% w/w solution of ammonium pelargonate (AP). After 1 day, the necrosis in the control plot was 0% while in the glyphosate plus A.P. plot the necrosis was 35%. After 11 days the corresponding percentages were 25 and 85. After 23 days, necrosis on the control was 96% while the A.P. test plot was 98%. Thus, the addition of ammonium pelargonate to glyphosate reduced the time for necrotic symptoms to appear on fescue.

Example 4

The effect of adding ammonium pelargonate to a diphenylether-herbicide fomesafen (Syngenta tradename REFLEX®), was studied on the control of the weed velvetleaf. The velvetleaf was grown in pots, three plants to a pot. Each test was replicated three times on plants 7–8 inches tall. In the control test, Reflex was sprayed on the velvetleaf at a rate of 0.048 ai/A (0.19 pt/A) with a spray volume of 24 gpa. In the additive test, Reflex was dissolved in 0.5% w/w aqueous ammonium pelargonate solution and sprayed at the same 0.048 ai/A rate. After 4 days, the necrosis on the control plots was an average of 10% while on the plants sprayed with Reflex plus ammonium pelargonate, the average necrosis was 88%. The amount of Reflex used in these tests was ¼th the manufacturers recommended rate for weed control.

Example 5

The effect of adding ammonium pelargonate to a benzothiadiazole herbicide, bentazone (BASF tradename BASAGRAN®), was studied on the control of the weed velvetleaf. The velvetleaf were grown as described in Example 4, that is, 3 to a pot with the tests run on 7–8 inch plants and each test replicated three times. Basagran alone was applied at the rate of 0.5 pint of commercially supplied product per acre. The ammonium pelargonate additive effect was studied at the same application rate with the Basagran dissolved in 0.5% ammonium pelargonate solution. After 4 days, the average necrosis on the control pots was 7% while on the weeds treated with Basagran plus ammonium pelargonate, the necrosis was 42%. After 8 days, the corresponding necrosis observed were 35% and 53%. The amount of Basagran used was ¼th the manufacturers' recommended rate.

Example 6

The effect of adding ammonium pelargonate to a sulfonylurea herbicide, rimsulfuron (DuPont tradename MATRIX®), was studied on velvetleaf. The velvetleaf were planted 6 to a pot and at the time of the test were 3.5 to 5 inches tall. The tests were replicated three times. In the control test, Matrix was applied at the rate of 0.5 oz. of commercial product per acre. In the additive test, the Matrix was added to 0.5% ammonium pelargonate solution which was then applied at the same 0.5 oz. per acre rate. After 14 days the weed control was 18% in the control plots versus 43% in the additive plots. After 21 days, the corresponding percentages were 7 and 37. The amount of Matrix used was ¼th the manufacturers recommended rate.

Example 7

The effect of adding ammonium pelargonate to a cyclohexanedione herbicide, sethoxydim (BASF tradename POAST®), was studied on sweet corn in pots containing 4 corn plants per pot. Each test was replicated three times. In the control test, Poast was sprayed on the corn at the rate of 0.063 lb ai/A (⅓ pt) using an application rate of 24 gpa. The additive test was run with the Poast added to 0.5% ammonium pelargonate solution which was then sprayed at the same 0.063 lb ai/A rate on identical pots. After 4 days, the average corn control was 0% in the control plots while it was 27% in the additive plots. After ten days, the average corn control in the control plots was 43% while in the additive plots, it was 80%. After 15 days, the corresponding percentages were 13 and 88. The amount of Poast used was ⅓ the manufacturers' recommended rate.

Example 8

To test enhanced control of the weed velvetleaf with glyphosate, velvetleaf was grown in pots containing 2 plants/pot to a height of 10 to 14 inches. ROUNDUP CUSTOM® was sprayed on three pots at a rate of 1.0 lb. ai/A using a spray volume rate of 24 gpa. Another three pots were sprayed with the same concentration of ROUNDUP CUSTOM dissolved in 0.5% ammonium pelargonate solution (A.P.) while a third test was run using the same concentration of ROUNDUP CUSTOM in 0.3% ammonium pelargonate solution. The results were:

|  | % Control (Average) | |
| --- | --- | --- |
|  | After 13 days | After 26 days |
| Roundup | 96 | 82 |
| Roundup in 0.5% A.P. | 99 | 93 |
| Roundup in 0.3% A.P. | 95 | 97 |

Example 9

To test enhanced control of the weed ragweed with glyphosate, ragweed was grown in pots containing 1–2 plants per pot. When the plants were at the 5 pair of leaves stage with an average height of 7–8 inches, three pots were sprayed with ROUNDUP CUSTOM at a rate of 0.5 lb. ai/A using a spray volume of 24 gpa. Three more pots were sprayed at the same rate and volume with the ROUNDUP CUSTOM dissolved in 0.5% by weight ammonium pelargonate solution. After 25 days the observed control was an average of 73% with ROUNDUP CUSTOM alone while when dissolved in A.P. it was an average of 83%.

Example 10

To test enhanced control of the weed morningglory with glyphosate, morningglory was grown in pots, 3 plants/pot, to a 4 leaf stage and a height of 3.5–4.5 inches. Three pots were sprayed with ROUNDUP CUSTOM at an 0.5 lb. ai/A rate using a 24 gpa spray volume. Another three pots were sprayed at the same rate with ROUNDUP CUSTOM dissolved in 0.5% by weight ammonium pelargonate solution. The results were:

|  | % Control (Average) | | |
| --- | --- | --- | --- |
|  | After 5 days | After 14 days | After 25 days |
| Roundup | 30 | 40 | 50 |
| Roundup in 0.5% A.P. | 38 | 85 | 63 |

From the foregoing, it will be observed that numerous variations and modifications may be effected without departing from the true spirit and scope of the novel concepts of the invention.

What is claimed is:

1. A method for the prevention or elimination of undesired vegetation which comprises applying to the locus of the undesired vegetation a herbicidally effective amount of an aqueous solution wherein the herbicide of the solution consists essentially of a post-emergent herbicide and at least one compound represented by the formula:

$$R_1COO^-X^+ \quad (I)$$

wherein $R_1$ is a $C_7$ to $C_{11}$ hydrocarbyl group, optionally substituted with one or more hydroxyl or $C_1$–$C_5$ hydrocarbyl groups; and X is ammonium.

2. The method of claim 1, wherein the amount of compound represented by the formula (I) in the composition is between from about 0.10 to about 3.0 percent by weight.

3. The method of claim 2, wherein the amount of compound represented by the formula (I) in the composition is between from about 0.50 to about 1.0 percent by weight.

4. The method of claim 2, wherein the compound of formula (I) is an ammonium salt of caprylic, pelargonic, capric, undecanoic, or lauric acid.

5. The method of claim 4, wherein the compound of formula (I) is ammonium pelargonate.

6. The method of claim 2, wherein the composition contains a mixture of two or more compounds of the formula $R_1COO^-X^+$.

7. The method of claim 2, wherein $R_1$ is a saturated hydrocarbyl group.

8. The method of claim 2, wherein the aqueous solution further contains a diluent.

9. The method of claim 2, wherein the post-emergent herbicide is glyphosate.

10. The method of claim 2, wherein the post-emergent herbicide is a monoammonium or diammonium salt of glyphosate.

11. The method of claim 2, wherein the post-emergent herbicide is a sulfonylurea.

12. The method of claim 2, wherein the post-mergent herbicide is a cyclohexanedione.

13. The method of claim 2, wherein the post-emergent herbicide is a benzothiadiazole.

14. The method of claim 2, wherein the post-emergent herbicide is a diphenylether.

15. A herbicidal composition comprising a post-emergent herbicide and at least one compound represented by the formula:

$$R_1COO^-X^+ \quad (I)$$

wherein $R_1$ is a $C_7$ to $C_{11}$ hydrocarbyl group, optionally substituted
with one or more hydroxyl or $C_1$–$C_5$ hydrocarbyl groups; and X is ammonium; and further wherein the compound of formula (I) increases the herbicidal effect of the composition on the plant beyond that of a composition without the compound of formula (I).

16. The composition of claim 15, wherein the amount of the compound of formula (I) in the composition is between from about 0.10 to about 3.0 weight percent.

17. The composition of claim 16, wherein the amount of the compound of formula (I) in the composition is between from about 0.5 to about 1.0 percent by weight.

18. The composition of claim 16, wherein the compound of formula (I) is the ammonium salt of caprylic, pelargonic, capric, undecanoic, or lauric acid.

19. The composition of claim 18, wherein the compound of formula (I) is ammonium pelargonate.

20. The composition of claim 16, which contains a mixture of two or more compounds of the formula (I).

21. The composition of claim 16, wherein $R_1$ is a saturated hydrocarbyl group.

22. The composition of claim 16, wherein the post-emergent herbicide is a glyphosate.

23. The composition of claim 16, wherein the post-emergent herbicide is a monoammonium or diammonium salt of glyphosate.

24. The composition of claim 16, wherein the post-emergent herbicide is a sulfonylurea.

25. The composition of claim 16, wherein the post-emergent herbicide is a cyclohexanedione.

26. The composition of claim 16, wherein the post-emergent herbicide is a benzothiadiazole.

27. The composition of claim 16, wherein the post-emergent herbicide is a diphenylether.

28. A method of controlling plant growth which comprises applying to a plant a herbicidally effective amount of a herbicidal composition comprising a post-emergent herbicide and at least one compound represented by the formula:

$$R_1COO^-X^+ \qquad (I)$$

wherein $R_1$ is a $C_7$ to $C_{11}$ hydrocarbyl group, optionally substituted with one or more hydroxyl or $C_1$–$C_5$ hydrocarbyl groups; and X is ammonium, and further wherein the amount of compound of formula (I) is sufficient to increase the herbicidal effect of the composition beyond that of the composition without the compound of formula (I).

29. The method of claim 28, wherein the amount of the compound of formula (I) in the composition is between from about 0.10 to about 3.0 weight percent.

30. The method of claim 29, wherein the amount of the compound of formula (I) in the composition is between from about 0.50 to about 1.0 weight percent.

31. The composition of claim 29, wherein the composition contains a mixture of two or more compounds of the formula $R_1COO^-X^+$.

32. The method of claim 29, wherein the compound of formula (I) is an ammonium salt of caprylic, pelargonic, capric, undecanoic or lauric acid.

33. The method of claim 32, wherein the compound of formula (I) is ammonium pelargonate.

* * * * *